US010786176B2

(12) United States Patent
Nebuya

(10) Patent No.: US 10,786,176 B2
(45) Date of Patent: Sep. 29, 2020

(54) FAT THICKNESS ESTIMATING DEVICE, FAT THICKNESS ESTIMATING SYSTEM, FAT THICKNESS MEASURING METHOD, AND PROGRAM

(71) Applicant: SCHOOL JURIDICAL PERSON KITASATO INSTITUTE, Tokyo (JP)

(72) Inventor: Satoru Nebuya, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 526 days.

(21) Appl. No.: 15/123,341

(22) PCT Filed: Mar. 6, 2015

(86) PCT No.: PCT/JP2015/056649
§ 371 (c)(1),
(2) Date: Dec. 14, 2016

(87) PCT Pub. No.: WO2015/133604
PCT Pub. Date: Sep. 11, 2015

(65) Prior Publication Data
US 2017/0105652 A1    Apr. 20, 2017

(30) Foreign Application Priority Data

Mar. 7, 2014   (JP) ................................ 2014-045710

(51) Int. Cl.
*A61B 5/053*   (2006.01)
*A61B 5/107*   (2006.01)
*A61B 5/00*    (2006.01)

(52) U.S. Cl.
CPC ............ *A61B 5/0537* (2013.01); *A61B 5/002* (2013.01); *A61B 5/1075* (2013.01);
(Continued)

(58) Field of Classification Search
CPC .... A61B 5/0537; A61B 5/4872; A61B 5/1075
See application file for complete search history.

(56) References Cited

U.S. PATENT DOCUMENTS

| 7,203,536 B2 | 4/2007 | Masuo | |
|---|---|---|---|
| 8,099,160 B2 * | 1/2012 | Kanai | A61B 5/0537 |
| | | | 600/301 |

(Continued)

FOREIGN PATENT DOCUMENTS

| JP | 2000-139865 | 5/2000 |
|---|---|---|
| JP | 2001-149330 | 6/2001 |

(Continued)

OTHER PUBLICATIONS

Scharfetter et al, "Fat and Hydration Monitoring by Abdominal Bioimpedance Analysis: Data Interpretation by Hierarchical Electrical Modeling" IEEE Transactions on Biomedical Engineering, vol. 52, No. 6, Jun. 2005 p. 975 (Year: 2005).*

(Continued)

*Primary Examiner* — David J. McCrosky
(74) *Attorney, Agent, or Firm* — Nixon & Vanderhye P.C.

(57) ABSTRACT

A fat thickness estimating device includes a storage unit that stores information indicating relationship between fat thickness and ratio of bioelectrical impedance in a first condition and bioelectrical impedance in a second condition, a measured impedance value acquiring unit configured to acquire a measured impedance value in the first condition of a target living body and a measured impedance value in the second condition of the target living body, and an estimation unit configured to calculate a fat thickness value in the target living body based on the information and a ratio of the measured impedance value in the first condition and the measured impedance value in the second condition.

11 Claims, 9 Drawing Sheets

(52) U.S. Cl.
CPC .......... *A61B 5/4872* (2013.01); *A61B 5/6824* (2013.01); *A61B 5/6843* (2013.01); *A61B 5/7278* (2013.01); *A61B 2562/0209* (2013.01); *A61B 2562/029* (2013.01); *A61B 2562/0261* (2013.01); *A61B 2562/043* (2013.01); *A61B 2562/063* (2013.01)

(56) References Cited

U.S. PATENT DOCUMENTS

| | | | |
|---|---|---|---|
| 2001/0010467 A1 | 8/2001 | Oguma et al. | |
| 2006/0100532 A1 | 5/2006 | Bae et al. | |
| 2006/0282005 A1 | 12/2006 | Kasahara et al. | |
| 2010/0256516 A1* | 10/2010 | Kasahara | A61B 5/0537 600/547 |
| 2012/0330167 A1* | 12/2012 | Gaw | A61B 5/0537 600/481 |
| 2013/0158371 A1* | 6/2013 | Mineta | A61B 5/0537 600/305 |
| 2013/0172775 A1 | 7/2013 | Ozawa | |
| 2014/0018641 A1* | 1/2014 | Yoshino | A61B 5/01 600/301 |
| 2014/0031713 A1* | 1/2014 | Gaw | A61B 5/0537 600/547 |

FOREIGN PATENT DOCUMENTS

| | | |
|---|---|---|
| JP | 2001-178697 | 7/2001 |
| JP | 2001-212098 | 8/2001 |
| JP | 2003-169785 | 6/2003 |
| JP | 2006-288735 | 10/2006 |
| JP | 2006-305218 | 11/2006 |
| JP | 2006-334325 | 12/2006 |
| JP | 2010-526604 | 8/2010 |
| JP | 2011-251158 | 12/2011 |
| JP | 2012-176063 | 9/2012 |
| JP | 2012-183253 | 9/2012 |
| JP | 2013-126458 | 6/2013 |
| JP | 2013-150790 | 8/2013 |
| JP | 2013-183767 | 9/2013 |
| WO | WO 2008/138062 | 11/2008 |
| WO | WO 2013/140725 | 9/2013 |

OTHER PUBLICATIONS

European Search Resort issued in Appln. No. 15758077.0 dated Oct. 17, 2017.

International Search Report issued in PCT/JP2015/056649 dated Apr. 7, 2015.

Office Action issued in JP Appln. No. 2016-506569 dated Feb. 26, 2019 (w/ translation).

* cited by examiner

FAT THICKNESS ESTIMATING DEVICE, FAT THICKNESS ESTIMATING SYSTEM, FAT THICKNESS MEASURING METHOD, AND PROGRAM

This application is the U.S. national phase of International Application No. PCT/JP2015/056649 filed 6 Mar. 2015 which designated the U.S. and claims priority to JP Patent Application No. 2014-045710 filed 7 Mar. 2014, the entire contents of each of which are hereby incorporated by reference.

TECHNICAL FIELD

The present invention relates to a fat thickness estimating device, a fat thickness measuring system, a fat thickness estimating method, and a program.

Priority is claimed on Japanese Patent Application No. 2014-045710, filed Mar. 7, 2014, the content of which is incorporated herein by reference.

BACKGROUND

As a method of measuring a fat thickness value (a thickness of fat) of a living body, a method of estimating a fat thickness value by causing a current to flow into a living body, measuring impedance (bioelectrical impedance) in the living body, and estimating the fat thickness value from the measured impedance value is known.

Regarding such measurement of body fat using a current, in a trunk visceral fat measuring method described in Patent Document 1, bioelectrical impedance of the trunk is measured at a first frequency, bioelectrical impedance of the trunk is measured at a second frequency higher than the first frequency, an internal organic tissue volume of the trunk is calculated on the basis of somatic specification information, impedance of internal organic tissue of the trunk is calculated on the basis of the calculated internal organic tissue volume of the trunk and the somatic specification information, impedance of trunk visceral fat tissue is calculated on the basis of the bioelectrical impedance of the trunk measured at the first frequency and the second frequency and the calculated impedance of the trunk visceral fat tissue, and a trunk visceral fat tissue volume is calculated on the basis of the calculated impedance of the trunk visceral fat tissue and the somatic specification information.

RELATED ART DOCUMENTS

Patent Document

[Patent Document 1]
Japanese Patent Application, Publication No. 2006-288735

SUMMARY OF INVENTION

Technical Problem

When contact of a current injection electrode or an impedance measurement electrode with a living body is not sufficient at the time of measuring impedance by causing a current to flow into the living body, impedance of the contact part increases and thus bioelectrical impedance cannot be accurately measured.

Particularly, when a thickness of subcutaneous fat in a part of a living body such as an abdomen or an upper arm is estimated, pressing an electrode down against an estimation target part to measure impedance can be considered. In this case, like the trunk visceral fat measuring method described in Patent Document 1, the contact of an electrode with a living body is likely to be more uneven than that when a living body (such as a person) is put on the device and there is a possibility of an influence on measurement of bioelectrical impedance.

The present invention provides a fat thickness estimating device, a fat thickness estimating system, a fat thickness estimating method, and a program that can obtain stable accuracy.

Solution to Problem

According to a first aspect of the present invention, there is provided a fat thickness estimating device including: a storage unit that stores information indicating relationship between fat thickness and ratio of bioelectrical impedance in a first condition and bioelectrical impedance in a second condition; a measured impedance value acquiring unit configured to acquire a measured impedance value in the first condition of a target living body and a measured impedance value in the second condition of the target living body; and an estimation unit configured to calculate a fat thickness in the target living body based on the information and a ratio of the measured impedance value in the first condition and the measured impedance value in the second condition.

The information may include information indicating relationship between fat thickness and ratio of bioelectrical impedance based on a current of a first frequency and bioelectrical impedance based on a second frequency higher than the first frequency, and the estimation unit may be configured to acquire a measured impedance value based on the current of the first frequency as the measured impedance value in the first condition and to acquire a measured impedance value based on the current of the second frequency as the measured impedance value in the second condition.

The fat thickness estimating device may further include: a detection unit configured to detect a contact state of the pair of electrodes, which is used in impedance measurement, with the living body; and a display unit configured to display a detection result of the detection unit along a time.

The fat thickness estimating device may further include: a detection unit configured to detect a variation coefficient of the measured impedance value of the target living body or of a value based on the measured impedance value; and a display unit configured to display the variation coefficient.

The fat thickness estimating device may further include a moisture estimating unit configured to estimate the degree of moisture of skin of the living body on the basis of the measured impedance value of the living body.

According to a second aspect of the present invention, there is provided a fat thickness estimating system including an impedance measuring unit and a fat thickness estimating device, wherein the impedance measuring unit is configured to measure impedance in a first condition of a target living body and impedance in a second condition of the target living body, and the fat thickness estimating device includes: a storage unit that stores information indicating relationship between fat thickness and ratio of bioelectrical impedance in the first condition and bioelectrical impedance in the second condition and a fat thickness; a measured impedance value acquiring unit configured to acquire a measured impedance value in the first condition and a measured impedance value in the second condition which are measured by the impedance measuring unit; and an estimation unit configured to estimate a fat thickness value of the target living body based on the information and on a ratio of the measured impedance value in the first condition and the measured impedance value in the second condition.

The impedance measuring unit may include a plurality of pairs of electrodes having different intervals, the information may include information indicating relationships each between fat thickness and ratio of bioelectrical impedance based on a current of a first frequency and bioelectrical impedance based on a current of a second frequency via any one of the plurality of pairs of electrodes, which is selected according to fat thickness, and the estimation unit may be configured to estimate a fat thickness value of the target living body on the basis of a ratio, which is correlated with fat thickness in the information, among ratios of the bioelectrical impedance based on the current of the first frequency and the bioelectrical impedance based on the current of the second frequency which are measured by the plurality of pairs of electrodes.

According to a third aspect of the present invention, there is provided a fat thickness estimating method including: a measured impedance value acquiring step of acquiring a measured impedance value in a first condition of a target living body and a measured impedance value in a second condition of the target living body; and a fat thickness estimating step of estimating a fat thickness value of the target living body based on a ratio of the measured impedance value in the first condition and the measured impedance value in the second condition and on information indicating relationship between fat thickness and ratio of bioelectrical impedance in the first condition and bioelectrical impedance in the second condition.

According to a fourth aspect of the present invention, there is provided a program causing a computer to perform: a measured impedance value acquiring step of acquiring a measured impedance value in a first condition of a target living body and a measured impedance value in a second condition of the target living body; and a fat thickness estimating step of estimating a fat thickness value of the target living body based on a ratio of the measured impedance value in the first condition and the measured impedance value in the second condition and on information indicating relationship between fat thickness and ratio of bioelectrical impedance in the first condition and bioelectrical impedance in the second condition.

Advantageous Effects of Invention

According to the present invention, it is possible to estimate a fat thickness value with stable accuracy.

DESCRIPTION OF EMBODIMENTS

Hereinafter, embodiments of the present invention will be described, but the following embodiments will not define the invention described in the appended claims. Not all combinations of features which are described in the embodiments are essential for solving the present invention.

Figure 1:
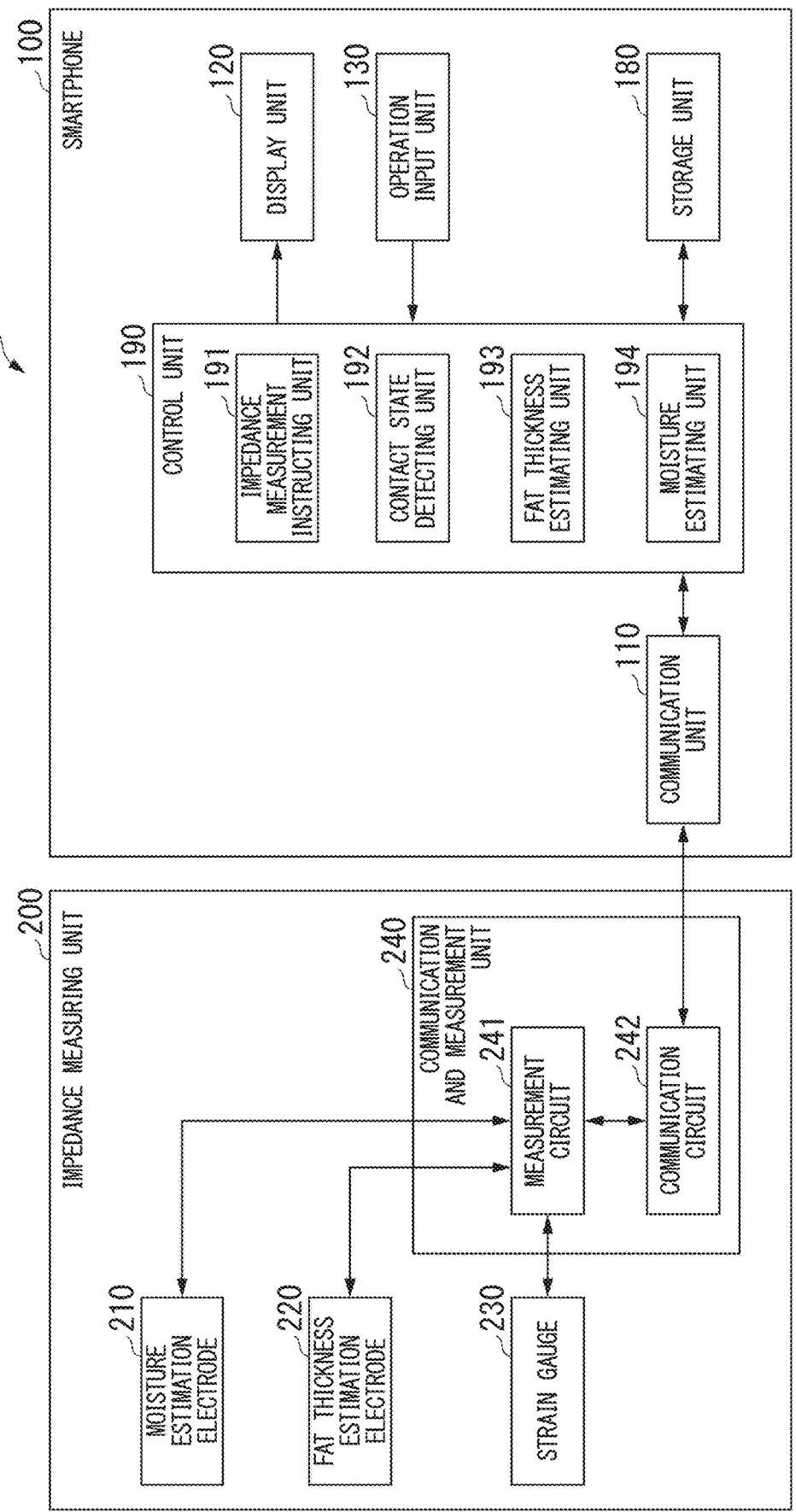
FIG. 1 is a block diagram schematically showing a functional configuration of a fat thickness estimating system according to an embodiment of the present invention.

FIG. 1 is a block diagram schematically showing a functional configuration of a fat thickness estimating system according to an embodiment of the present invention. In the drawing, the fat thickness estimating system 1 includes a smartphone (a portable information terminal, a tablet terminal, or a mobile computer) 100 and an impedance measuring unit 200. The smartphone 100 includes a communication unit 110m, a display unit 120, an operation input unit 130, a storage unit 180, and a control unit 190. The control unit 190 includes an impedance measurement instructing unit 191, a contact state detecting unit (a detection unit) 192, a fat thickness estimating unit (an estimation unit, a calculation unit) 193, and a moisture estimating unit (a calculation unit) 194. The impedance measuring unit (a measured impedance value acquiring unit) 200 includes a moisture estimation electrode 210, a fat thickness estimation electrode 220, a strain gauge (e.g., a detector, a contact strength sensor) 230, and a measurement and communication unit (a measured impedance value acquiring unit) 240. The measurement and communication unit 240 includes a measurement circuit 241 and a communication circuit 242.

The fat thickness estimating system 1 is a system for measuring a subcutaneous fat thickness value of a living body. The fat thickness estimating system 1 measures the subcutaneous fat thickness value by injecting a current into the living body to measure impedance and estimating the subcutaneous fat thickness value from the measured impedance value. For example, the fat thickness estimating system 1 estimates a subcutaneous fat thickness value of a certain part such as an abdomen or an upper arm of a person.

The subcutaneous fat thickness value mentioned herein is a thickness of subcutaneous fat. Hereinafter, the subcutaneous fat thickness value is simply referred to as a "fat thickness."

In this embodiment, it is assumed that a living body of which a fat thickness is estimated (a target living body) is human. Specifically, the fat thickness estimating system 1 estimates (measures, calculates) a fat thickness of a user of the fat thickness estimating system 1.

In this embodiment, the fat thickness estimating system 1 estimates the fat thickness on the basis of a measured voltage value when a constant current is injected into a living body. When a constant current is injected, impedance appears in the measured voltage value.

The impedance measuring unit 200 measures impedance in response to an instruction from the smartphone 100. Specifically, the impedance measuring unit 200 receives an impedance measurement instruction from the smartphone 100 in a state in which the impedance measuring unit is in contact with skin of a user and measures impedance in response to the instruction.

Particularly, the impedance measuring unit 200 measures impedance based on a current of a first frequency and impedance based on a current of a second frequency in a living body of which fat thickness is estimated (a target living body, a user). As will be described later, by standardizing the impedance based on the current of the first frequency which is relatively low using the impedance based on the current of the second frequency which is relatively high as a reference value, an influence of a contact state of the impedance measuring unit 200 with skin to the impedance can be reduced.

The impedance measuring unit 200 (the fat thickness estimation electrode 220) includes a plurality of pairs of current injection electrodes having different intervals as will be described later with reference to FIG. 2. The impedance measuring unit 200 injects a current into a living body from the current injection electrode instructed from the smartphone 100 and measures impedance. The current is selectively applied to two or more electrodes (application electrodes) of the plurality of pairs of electrodes on the basis of the instruction from the smartphone 100. As will be described later, by properly using the pairs of electrodes having different intervals, it is possible to estimate a fat thickness with higher accuracy when fat is thin or thick.

The impedance measuring unit 200 measures impedance for estimation of a degree of moisture of skin in response to an instruction from the smartphone 100.

The moisture estimation electrode 210 is an impedance measurement electrode for estimation of a degree of moisture of skin. Details of the moisture estimation electrode 210 will be described later with reference to FIG. 2.

The fat thickness estimation electrode 220 is an impedance measurement electrode for estimation of a fat thickness. Details of the fat thickness estimation electrode 220 will be described later with reference to FIG. 2.

The strain gauge (the contact strength sensor) 230 is a sensor for measuring strength (degree, level, pressure) with which the impedance measuring unit 200 comes in contact with a living body. Here, by pressing the impedance measuring unit 200 against the living body, for example, a warp corresponding to the shape of the living body such as a convex shape of an arm is generated in the strain gauge 230. The strain gauge 230 measures a strain due to the warp. The measured strain value measured by the strain gauge 230 is used as a value (an index) indicating strength with which the impedance measuring unit 200 comes in contact with the living body.

When the strain gauge 230 is pressed against the living body, the living body (a measurement part such as an upper arm) is pressed and deformed and there is a possibility of a pressure not being accurately measured. Therefore, a protrusion having a small convex shape may be disposed on a contact surface of the strain gauge 230 with a living body. When the strain gauge 230 is pressed against the living body, the strain gauge 230 is pressed and warped by the protrusion and it is thus expected to measure a pressure.

Alternatively, similarly to the structure of a general pressure sensor, the strain gauge 230 may measure a pressure using a method other than the method of disposing the protrusion, for example, fixing the strain gauge 230 to a plate or the like to generate a warp corresponding to the pressure in the strain gauge 230.

Similarly to the case in which the fat thickness is measured, when a degree of moisture of skin is measured, the strength (pressure) with which the moisture estimation electrode 210 comes in contact with skin may also be measured by a strain gauge or the like. For example, the same strain gauge as the strain gauge 230 may be disposed in the vicinity of the moisture estimation electrode 210.

In the measurement and communication unit 240, the measurement circuit 241 measures impedance in response to an impedance measurement instruction from the smartphone 100. Specifically, when an impedance measurement instruction to estimate a fat thickness is received from the smartphone 100 via the communication circuit 242, the measurement circuit 241 measures impedance using the fat thickness estimation electrode 220. When an impedance measurement instruction to estimate moisture is received from the smartphone 100 via the communication circuit 242, the measurement circuit 241 measures impedance using the moisture estimation electrode 210. The measurement circuit 241 transmits the measured impedance values to the smartphone 100 via the communication circuit 242.

The measurement circuit 241 acquires the measured strain value measured by the strain gauge 230 and transmits the acquired measured strain value to the smartphone 100 via the communication circuit 242.

The communication circuit 242 communicates with the smartphone 100 (the communication unit 110). Particularly, the communication circuit 242 receives an impedance measurement instruction from the smartphone 100. The communication circuit 242 transmits the measured impedance value measured by the measurement circuit 241 or the measured strain value measured by the strain gauge 230 to the smartphone 100.

Various communication modes can be employed as a communication mode between the impedance measuring unit 200 (the communication circuit 242) and the smartphone 100 (the communication unit 110). For example, the impedance measuring unit 200 and the smartphone 100 may communicate with each other in a short-range wireless communication method such as Bluetooth (registered trademark) or Wi-Fi (registered trademark), but are not limited thereto.

The smartphone 100 estimates a fat thickness or estimates a degree of moisture of skin using the impedance measuring unit 200 by executing a fat thickness estimating application. The smartphone 100 corresponds to an example of the fat thickness estimating device.

Here, a device other than the smartphone (such as a portable information terminal, a tablet terminal, or a mobile computer) 100 may be used as the fat thickness estimating device. For example, various information processing devices that can communicate with the impedance measuring unit 200, such as a personal computer (PC), can be used as the fat thickness estimating device.

The communication unit 110 communicates with the impedance measuring unit 200 (the communication circuit 242). Particularly, the communication unit 110 transmits an impedance measurement instruction from the impedance measurement instructing unit 191 to the impedance measuring unit 200. The communication unit 110 receives a measured impedance value or a measured strain value from the impedance measuring unit 200. The communication unit 110 acquires a measured impedance value based on a current of a first frequency which is a relatively low frequency and a measured impedance value based on a current of a second frequency which is a relatively high frequency as a measured impedance value for estimation of a fat thickness. The communication unit 110 corresponds to an example of the measured impedance value acquiring unit.

The display unit 120 includes a display screen such as a liquid crystal panel and displays various images such as a moving image, a still image, and text (characters). Particularly, the display unit 120 displays an estimated fat thickness value calculated from the measured impedance value by the fat thickness estimating unit 193 as a measured fat thickness value. The display unit 120 displays the detection result of the contact state (a close contact state, an arranged state, an approaching state, and a padding state) from the contact state detecting unit 192 along a time. As will be described later, the display of the detection result of the contact state along the time is used as an indicator indicating appropriateness of the method of pressing the impedance measuring unit 200 against a user's skin.

The operation input unit 130 includes an input device such as a touch sensor which is disposed on, for example, the display screen of the display unit 120 to constitute a touch panel and receives a user operation. Particularly, the operation input unit 130 receives a user operation of instructing to measure a fat thickness or a user operation indicating a part (such as an abdomen or an upper arm) of a fat thickness measurement target. The operation input unit 130 receives a user operation of instructing to measure the degree of moisture.

The storage unit 180 is constituted by a storage device of the smartphone 100 and stores a variety of information. Particularly, the storage unit 180 stores conversion data for calculating a fat thickness from impedance measurement results. More specifically, the storage unit 180 stores fat thickness acquiring information (a conversion table or a conversion equation) indicating relationship between fat thickness and ratio of bioelectrical impedance based on a current of a first frequency and bioelectrical impedance based on a current of a second frequency in advance.

Here, by calculating the ratio of the bioelectrical impedance based on the current of the first frequency and the bioelectrical impedance based on the current of the second frequency, the impedance based on the current of the first frequency is standardized with the impedance based on the current of the second frequency as a reference value.

Hereinafter, the ratio of the bioelectrical impedance based on the current of the first frequency and the bioelectrical impedance based on the current of the second frequency is referred to as an "impedance ratio."

The storage unit 180 stores the fat thickness acquiring information for a plurality of pairs of current injection electrodes having different intervals in the fat thickness estimation electrode 220 in advance. More specifically, the storage unit 180 stores information (a conversion table or a conversion equation) indicating relationship between fat thickness and impedance ratio based on any one of the plurality of pairs of current injection electrodes selected for each fat thickness as the fat thickness acquiring information.

The storage unit 180 stores the fat thickness acquiring information for each part of a body (such as an abdomen or an upper arm). The fat thickness estimating unit 193 can more accurately estimate the fat thickness using the fat thickness acquiring information corresponding to the measurement place indicated by a user operation.

The storage unit 180 stores moisture acquiring information (a conversion table or a conversion equation) for converting the measured impedance value measured using the moisture estimation electrode 210 by the measurement circuit 241 into the degree of moisture in advance. The degree of moisture in the moisture acquiring information may be indicated by a sensory expression (language) such as "moist" or "dry" or may be indicated by a numerical value.

The control unit 190 controls the units of the smartphone 100 to perform various functions. The control unit 190 is constituted by causing a central processing unit (CPU) of the smartphone 100 to read and execute a program from the storage unit 180.

The impedance measurement instructing unit 191 issues an impedance measurement instruction on the basis of the user operation received by the operation input unit 130, and transmits the impedance measurement instruction to the impedance measuring unit 200 via the communication unit 110. More specifically, when the operation input unit 130 receives the user operation instructing to measure a fat thickness and then the contact state detecting unit 192 detects that the pressing state of the impedance measuring unit 200 against the skin is good, the impedance measurement instructing unit 191 issues an impedance measurement instruction to estimate a fat thickness and transmits the impedance measurement instruction to the impedance measuring unit 200 via the communication unit 110. When the operation input unit 130 receives the user operation instructing to measure the degree of moisture of the skin and then the contact state detecting unit 192 detects that the pressing state of the impedance measuring unit 200 against the skin is good, the impedance measurement instructing unit 191 issues an impedance measurement instruction to estimate the degree of moisture and transmits the impedance measurement instruction to the impedance measuring unit 200 via the communication unit 110.

The contact state detecting unit 192 detects a contact state of the fat thickness estimation electrode 220 with the living body (the user). Details of the process which is performed by the contact state detecting unit 192 will be described later.

The fat thickness estimating unit 193 calculates a fat thickness in a target living body (a user) on the basis of the impedance ratio and the fat thickness acquiring information.

Here, as described above, the impedance ratio is a ratio of bioelectrical impedance based on the current of the first frequency and bioelectrical impedance based on the current of the second frequency. The second frequency is a higher frequency than the first frequency. As will be described later, a current of a higher frequency more easily flows in a living body than a current of a lower frequency does. Accordingly, in comparison with the current of a lower frequency, the measured impedance value based on the current of a higher frequency is less likely to be affected by tissue in a living body such as fat or muscle. On the other hand, in both a case in which the current has a relatively higher frequency and a case in which the current has a relatively lower frequency, the impedance is affected by the contact state of the impedance measuring unit 200 with the skin.

Therefore, by standardizing the impedance based on the current of the first frequency which is a relatively low frequency using the impedance based on the current of the second frequency which is a relatively high frequency as a reference value, it is possible to reduce an influence of the contact state of the impedance measuring unit 200 with the skin on the impedance. Specifically, the fat thickness estimating system 1 estimates a fat thickness using a ratio obtained by dividing the impedance based on the current of the first frequency by the impedance based on the current of the second frequency.

The fat thickness estimating unit 193 estimates the fat thickness of the target living body on the basis of the ratio, which is correlated with fat thickness in the fat thickness acquiring information, among impedance ratios by the plurality of pairs of current injection electrodes. Details of the process will be described later.

The moisture estimating unit 194 estimates the degree of moisture of the skin of the living body on the basis of the measured impedance value of the living body (the user). More specifically, the moisture estimating unit 194 estimates the degree of moisture of the skin on the basis of the measured impedance value measured using the moisture estimation electrode 210 and the moisture acquiring information.

Figure 2:
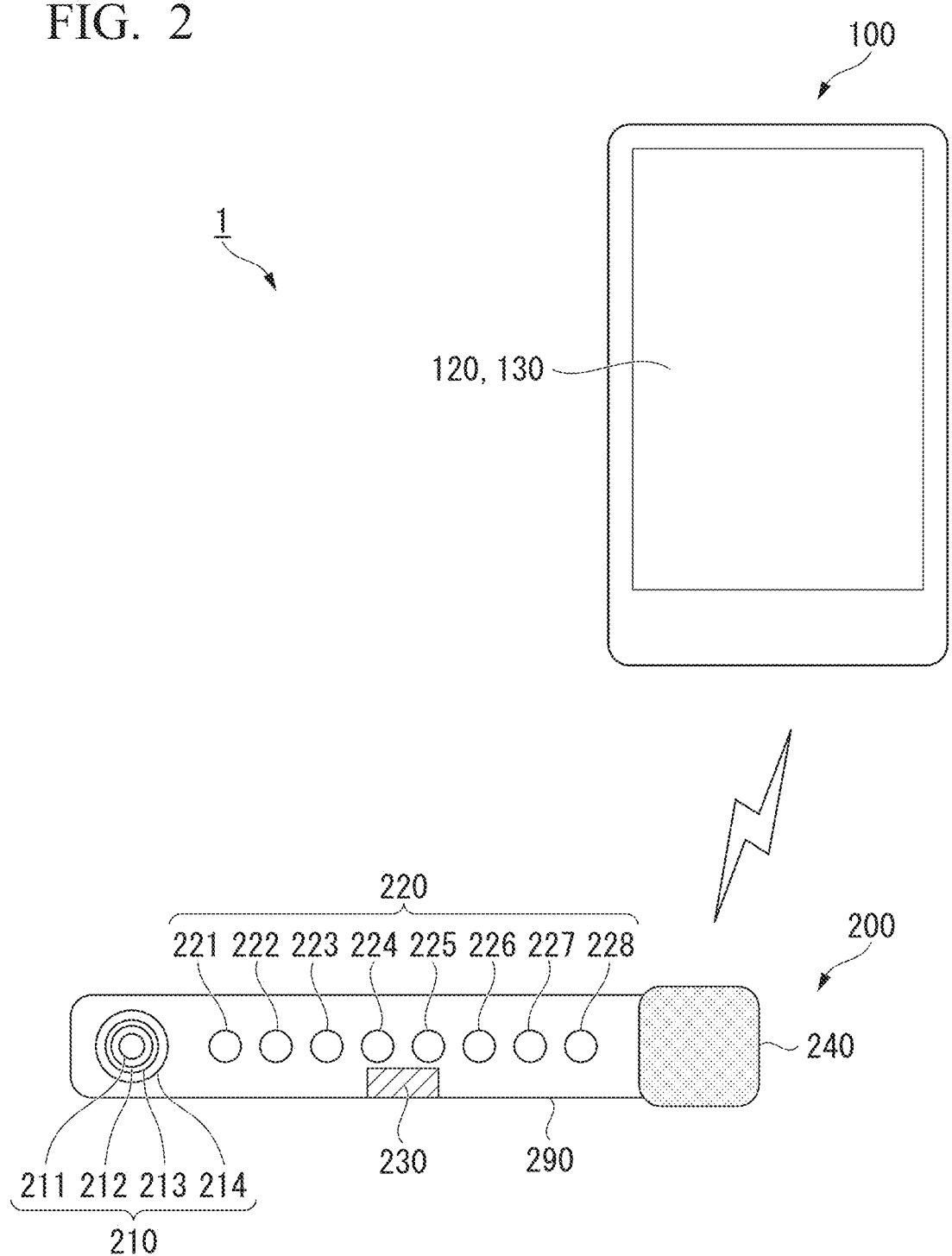
FIG. 2 is a diagram schematically showing a system configuration of the fat thickness estimating system according to the embodiment.

FIG. 2 is a diagram schematically showing a system configuration of the fat thickness estimating system 1. In the drawing, a touch panel in which the display screen of the display unit 120 and the touch sensor of the operation input unit 130 are combined is shown for the smartphone 100.

In the impedance measuring unit 200, a main body (such as a flexible member, a rigid member, a flexible card, a rigid card, a small-sized member, a pad member, a sheet member, a belt-like member, a belt-like member having flexibility, or a belt-like fabric) 290 is provided with a case in which the moisture estimation electrode 210, the fat thickness estimation electrode 220, the strain gauge 230, and the measurement and communication unit 240 (the measurement circuit 241 and the communication circuit 242) are disposed. The units are sewn onto, for example, fabric 290. For example, the units are electrically connected to each other by conductive threads sewn to the fabric 290. Alternatively, for example, the units of the impedance measuring unit 200 may be realized using a printed pattern in the main body 290 such as a printed board (which includes a flexible board, a rigid board, a flexible card, a rigid card, a small-sized board, a card board, a pad board, or a sheet board). The main body 290 is configured to be deformable (a) in a folded state (which includes a roll shape or a bent state) and (b) in a shape substantially corresponding to an outline of a target living body. Alternatively, the main body 290 is configured to be deformable (a) in a flat-plate shape and (b) in a shape substantially corresponding to an outline of a target living body (such as a circle-like shape or an ellipse-like shape). If the main body 290 has (a) a small size (such as a palm size, a card type, or a pad type) and/or is deformable in a folded state or in a flat-plate shape, it is advantageous for portability, versatility, and/or operability. In an alternative embodiment, a configuration in which at least a part of the moisture estimation electrode 210, the fat thickness estimation electrode 220, the strain gauge 230, and the measurement and communication unit 240 is omitted or a configuration in which at least a part thereof is disposed separately from the main body 290 may be configured.

The moisture estimation electrode 210 is configured to include four electrodes 211 to 214 having circular shapes or ring shapes. Among these electrodes, the innermost electrode 211 and the outermost electrode 214 are used as current injection electrodes, and the electrodes 212 and 213 therebetween are used as voltage detection electrodes. Specifically, the measurement circuit 241 (FIG. 1) measures moisture estimation impedance by a four-electrode method using the electrodes 211 to 214.

The fat thickness estimation electrode 220 is configured to include eight electrodes 221 to 228. For example, the electrodes are arranged in a line shape at intervals of 0.5, 1, 2, 3, 4, 5, 6, 7, 8, 9, 10, 15, or 20 millimeters (mm). The interval of the electrodes may be set to be less than 0.5 millimeters or equal to or greater than 20 millimeters. Among these eight electrodes, the outermost electrodes 221 and 228, the electrodes 222 and 227 therebetween, and the electrodes 223 and 226 therebetween are used as pairs of current injection electrodes. The innermost electrode 224 and 225 are used as a pair of voltage detection electrodes.

The number of units, the shapes thereof, or the arrangement thereof shown in FIG. 2 is merely an example and the present invention is not limited to the example. For example, the number of electrodes included in the fat thickness estimation electrode 220 is not limited to the eight shown in the drawing, but the total number of electrodes has only to be equal to or greater than four to include two or more current injection electrodes and two or more voltage measurement electrodes. When the pairs of electrodes are fixed, the fat thickness estimation electrode 220 is configured to have an even number of electrodes.

The current injection electrodes (application electrodes) do not need to include combinations of two (pairs of) electrodes but may include three or more electrodes. For example, the fat thickness estimating system 1 may power supplies between the electrodes 221 and 224 and between the electrodes 224 and 228 and may inject a current using the three electrodes as the current injection electrodes (application electrodes). Alternatively, the fat thickness estimating system 1 may inject a three-phase AC current using three electrodes as the current injection electrodes (application electrodes).

The voltage measurement electrodes (detection electrodes) do not need to include combinations of two (pairs of) electrodes but may include three or more electrodes. For example, the fat thickness estimating system 1 may simultaneously measure a voltage between the electrodes 224 and 225 and a voltage between the electrodes 225 and 226 using the electrodes 224, 225, and 226 as the voltage measurement electrodes (detection electrodes).

The moisture estimation electrode is not limited to the configuration shown in FIG. 2.

Figure 3:
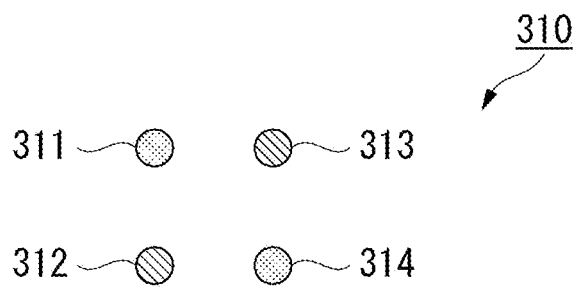
FIG. 3 is a diagram showing an example of a configuration of moisture estimation electrodes in the embodiment.

FIG. 3 is a diagram showing another example of the configuration of the moisture estimation electrode. In the drawing, a moisture estimation electrode 310 includes four electrodes 311 to 314. Among these electrodes, the electrodes 311 and 314 are used as the current injection electrodes (application electrodes) and the electrodes 312 and 313 are used as the voltage measurement electrodes (detection electrodes). The moisture estimation electrode 310 can be more easily sewn to a fabric 290 so as not to bring the electrodes into contact with each other than the moisture estimation electrode 210 can.

The fat thickness estimating system 1 may be embodied by a single device. For example, the impedance measuring unit 200 may have the units of the smartphone 100 shown in FIG. 1.

Alternatively, the fat thickness estimating system 1 may be embodied by three or more devices.

A relationship between an interval of electrodes or a frequency and a depth which a current reaches will be described below with reference to FIGS. 4 to 12.

Figure 4:
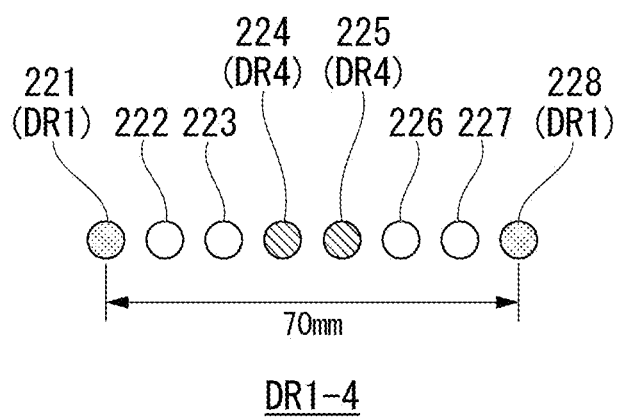
FIG. 4 is a diagram showing a first example in which electrodes are selected among fat thickness estimation electrodes in the embodiment.

FIG. 4 is a diagram showing a first example in which electrodes in the fat thickness estimation electrode 220 are selected.

In the drawing, the outermost electrodes 221 and 228 are used as the current injection electrodes, and the innermost electrodes 224 and 225 are used as the voltage measurement electrodes. In this case, the impedance measuring unit 200 injects a current at intervals of 70 millimeter. The example shown in FIG. 4 is an example in which the interval between the current injection electrodes is relatively large.

Hereinafter, positions of electrodes selected in the fat thickness estimation electrode 220 are denoted by DRx-y. Here, "x" indicates the position of the current injection electrode counted with the outermost electrodes (the electrodes 221 and 228) as 1. "y" indicates the position of the voltage detection electrode counted with the outermost electrodes as 1. The electrodes selected in FIG. 4 are denoted by "DR1-4."

Figure 5:
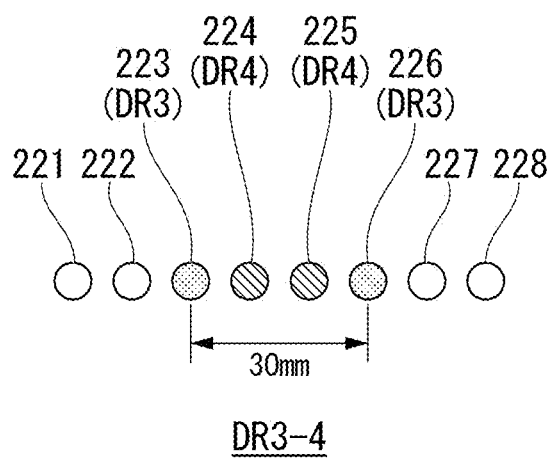
FIG. 5 is a diagram showing a second example in which electrodes are selected among fat thickness estimation electrodes in the embodiment.

FIG. 5 is a diagram showing a second example in which electrodes in the fat thickness estimation electrode 220 are selected. In the drawing, the third electrodes 223 and 226 from the outermost are used as the current injection electrodes and the innermost electrodes 224 and 225 are used as the voltage measuring electrodes. In this case, the impedance measuring unit 200 injects a current at intervals of 30 millimeter. The example shown in FIG. 5 is an example in which the interval of the current injection electrodes is relatively small.

The electrodes selected in FIG. 5 are denoted by "DR3-4."

Figure 6:
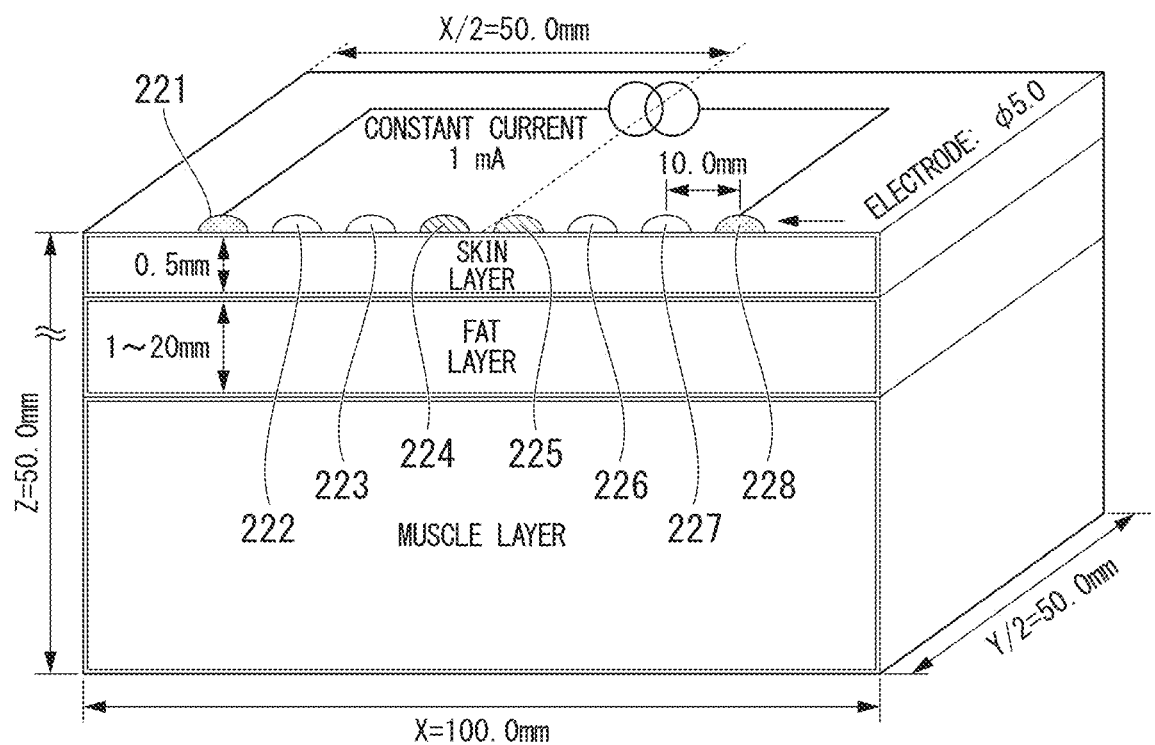
FIG. 6 is a diagram showing an example of a simulation model of a target living body in the embodiment.

FIG. 6 is a diagram showing an example of a simulation model for a target living body. In the simulation to be described below, as shown in the drawing, a biological model with a width (in an X direction) of 100 millimeter, a length (in a Y direction) of 100 millimeter, and a depth (in a Z direction) of 50 millimeter is constructed and a current distribution when a current is injected is simulated using a finite element method. In FIG. 6, a model in which the length is divided into halves (Y/2) is shown.

In the biological model, a skin layer, a fat layer, and a muscle layer are sequentially stacked from the uppermost and the thickness of the skin layer is set to 0.5 millimeters. The thickness of the fat layer is set to various values in a range of 0.5 millimeters to 20 millimeters. A point that the skin layer is set to be thicker than a general human skin is adjusted by setting characteristics of the skin layer.

As shown in FIG. 6, the electrodes 221 to 228 are set to a half position in length (Y/2) of the biological model and the center thereof is set to a half position in width (X/2). The interval of the electrodes is set to 10 millimeter.

In this model, a current distribution when a constant current of 1 mA is injected into a living body is simulated.

First, a relationship between a fat thickness and a current distribution will be described below.

Figure 7:
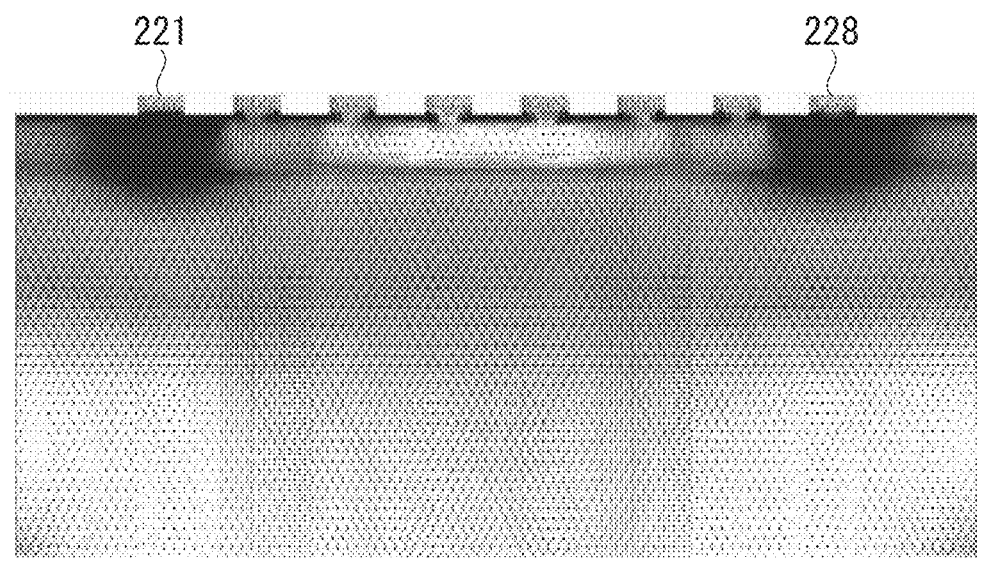
FIG. 7 is a diagram showing an example of a current distribution when a fat thickness is relatively small in the embodiment.

FIG. 7 is a diagram showing an example of a current distribution when a fat thickness is relatively small. The drawing shows a simulation result when the fat thickness (the thickness of the fat layer) is set to 5 millimeter and a current of 100 kHz is injected from the electrodes 221 and 228.

In FIGS. 7 to 12, amperage is expressed by light and shade. Specifically, the darker the light and shade becomes, the larger the amperage becomes and the lighter the light and shade becomes, the smaller the amperage becomes.

Figure 8:
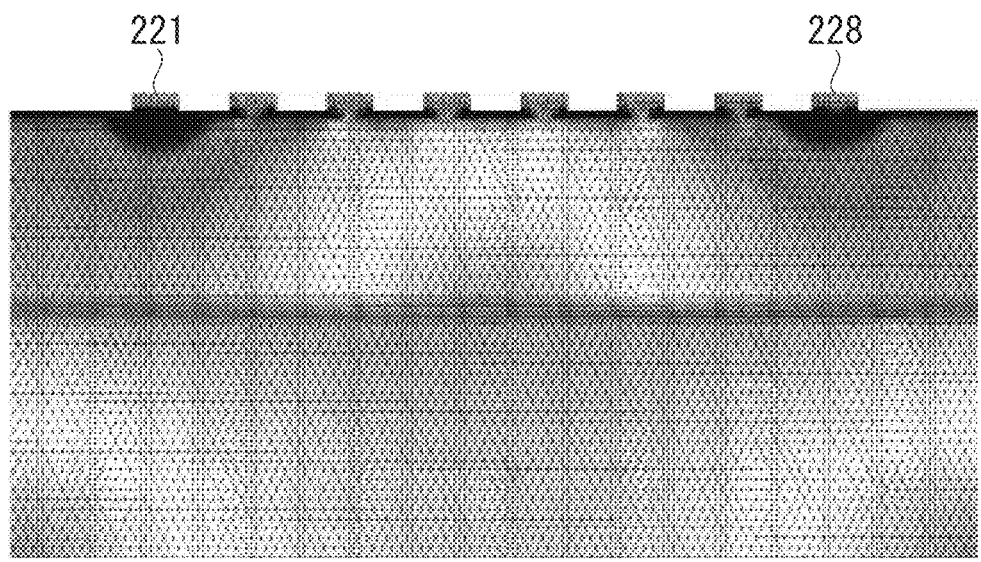
FIG. 8 is a diagram showing an example of a current distribution when a fat thickness is relatively large in the embodiment.

FIG. 8 is a diagram showing an example of a current distribution when a fat thickness is relatively large. The drawing shows a simulation result when the fat thickness is set to 10 millimeter. In the example shown in FIG. 8, similarly to the example shown in FIG. 7, the current injection electrodes are set to the electrodes 221 and 228 and the frequency of the current to be injected is set to 100 kHz.

By comparison of FIGS. 7 and 8, it can be seen that the current reaches a deeper region in the example shown in FIG. 7 in which the thickness of the fat layer is relatively small. This is because a current flows better in the muscle of the fat and the muscle.

In this way, when the fat thickness varies, the current distribution varies and the voltage measured by the voltage measurement electrodes also varies. Therefore, the contact state detecting unit 192 calculates the fat thickness on the basis of the measured voltage value.

A relationship between an interval of current injection electrodes and a current distribution will be described below.

Figure 9:
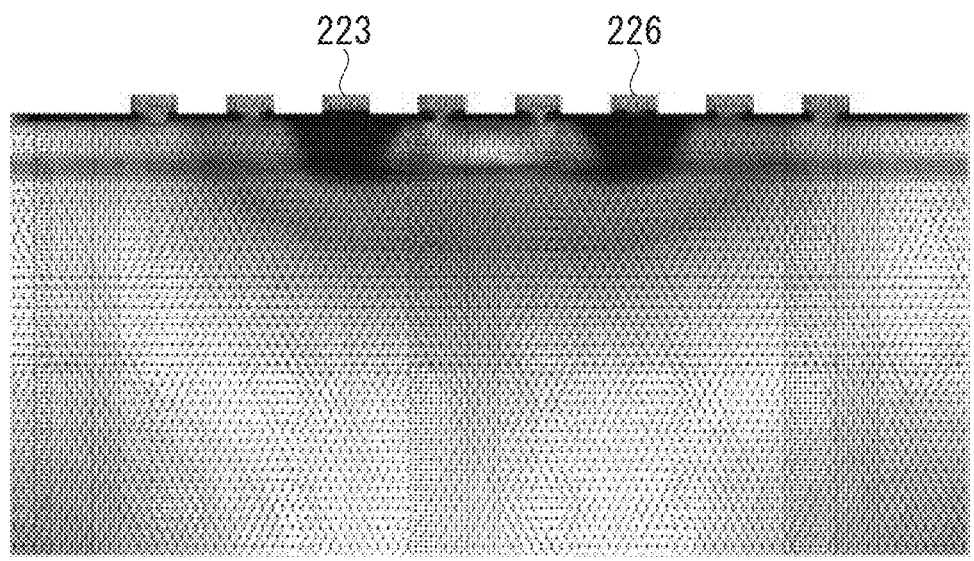
FIG. 9 is a diagram showing an example of a current distribution when an interval of current injection electrodes is relatively small in the embodiment.

FIG. 9 is a diagram showing an example of a current distribution when the interval of the current injection electrodes is relatively small. In the example shown in FIG. 7, the current injection electrodes are set to the electrodes 221 and 228 and the interval of the current injection electrodes is set to 70 millimeter, but in the example shown in FIG. 9, the current injection electrodes are set to the electrodes 223 and 226 and the interval of the current injection electrodes is set to 30 millimeter. On the other hand, similarly to the example shown in FIG. 7, in the example shown in FIG. 9, the fat thickness is set to 5 millimeter. Similarly to the example shown in FIG. 7, in the example shown in FIG. 9, the frequency of the current to be injected is set to 100 kHz.

By comparison of FIGS. 7 and 9, it can be seen that the current reaches a deeper region in the example shown in FIG. 7 in which the interval of the current injection electrodes is relatively large.

In this way, when the fat thickness is large, it is possible to more accurately estimate the fat thickness by setting the interval of the current injection electrodes to be larger. On the other hand, when the fat thickness is small, a difference of the measured voltage value increases with an increase in the difference of the fat thickness by setting the interval of the current injection electrodes to be smaller and it is thus possible to more accurately estimate the fat thickness.

Therefore, by properly using the interval of the current injection electrodes, the fat thickness estimating unit 193 can more accurately estimate the fat thickness when the fat thickness is small or large.

A relationship between a frequency of a current and a current distribution will be described below.

Figure 10:
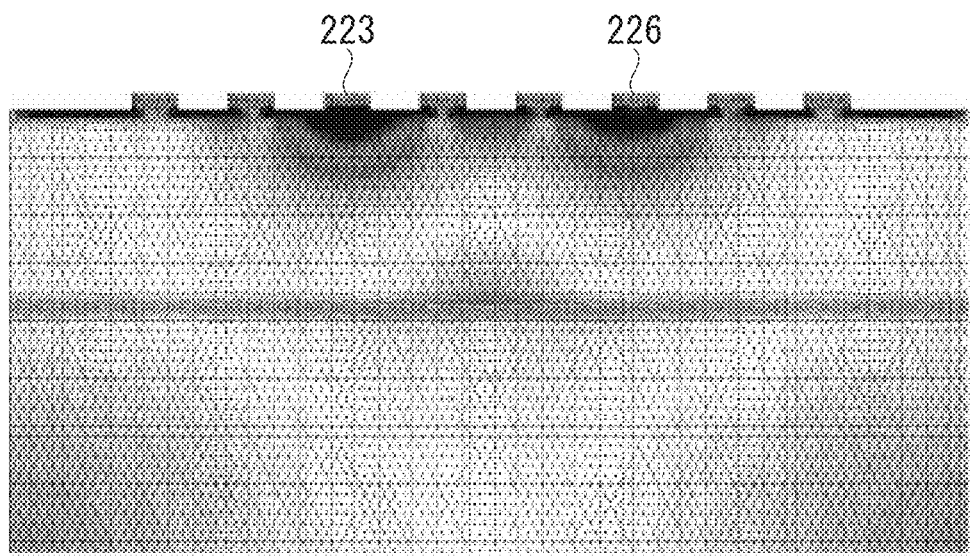
FIG. 10 is a diagram showing an example of a current distribution when a current having a relatively low frequency is injected in the embodiment.

FIG. 10 is a diagram showing an example of a current distribution when a current of a relatively low frequency is injected. The drawing shows a simulation result when the fat thickness is set to 20 millimeters and a current of 100 kHz is injected from the electrodes 223 and 226.

Figure 11:
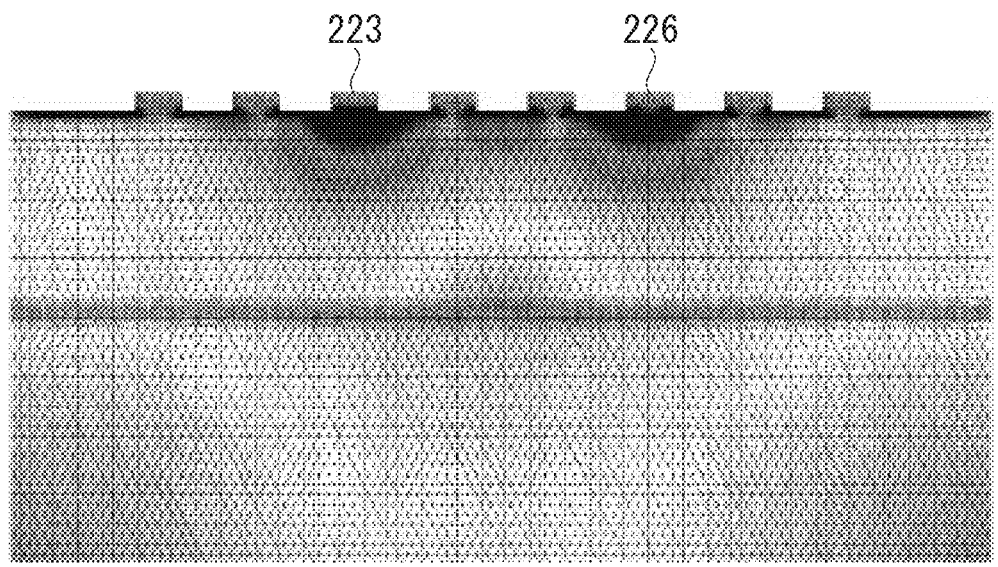
FIG. 11 is a diagram showing an example of a current distribution when a current having a relatively high frequency is injected in the embodiment.

FIG. 11 is a diagram showing an example of a current distribution when a current of a relatively high frequency is injected. In the example shown in FIG. 10, the frequency of the current is 100 kHz, but the example shown in FIG. 11 shows a simulation result when a current of 500 kHz is injected. On the other hand, similarly to the example shown in FIG. 10, in the example shown in FIG. 11, the fat thickness is 20 millimeter. Similarly to the example shown in FIG. 10, in the example shown in FIG. 11, the electrodes 223 and 226 are used as the current injection electrodes.

Figure 12:
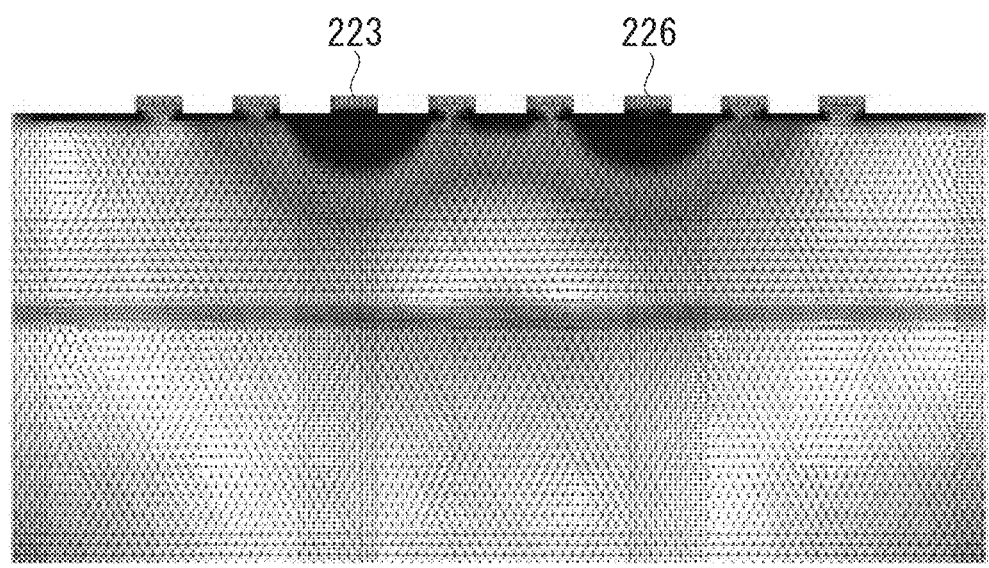
FIG. 12 is a diagram showing an example of a current distribution when a current having a much higher frequency is injected in the embodiment.

FIG. 12 is a diagram showing an example of a current distribution when a current of a higher frequency is injected. Unlike the example shown in FIG. 10 or the example shown in FIG. 11, the example shown in FIG. 12 shows a simulation result when a current of 1 MHz is injected. On the other hand, similarly to the example shown in FIG. 10 or the example shown in FIG. 11, in the example shown in FIG. 12, the fat thickness is set to 20 millimeter. Similarly to the example shown in FIG. 10 or the example shown in FIG. 11, in the example shown in FIG. 12, the electrodes 223 and 226 are used as the current injection electrodes.

By comparison of FIGS. 10 to 12, it can be seen that the higher the frequency of the current becomes, the deeper region the current reaches. In this way, when the frequency of the current is high, the fat thickness has a less influence and the measured voltage value measured by the voltage measurement electrodes is less likely to be affected by the impedance based on the fat thickness. On the other hand, when the frequency is high and when the frequency is low, the impedance is affected by the contact state of the electrodes with the skin (a pressing state of the impedance measuring unit 200 against the skin).

Accordingly, by standardizing the measured impedance value at a relatively low frequency with the measured impedance value at a relatively high frequency as a reference, it is possible to reduce an influence of the contact state of the electrodes with the skin to the impedance and to more accurately estimate the fat thickness.

Therefore, the fat thickness estimating unit 193 estimates the fat thickness using a ratio which is objected by the impedance based on the current of the first frequency which is relatively low by the impedance based on the current of the second frequency which is relatively high. The impedance is standardized by the division.

Proper use of the intervals of the current injection electrodes will be described below with reference to FIG. 13.

Figure 13:
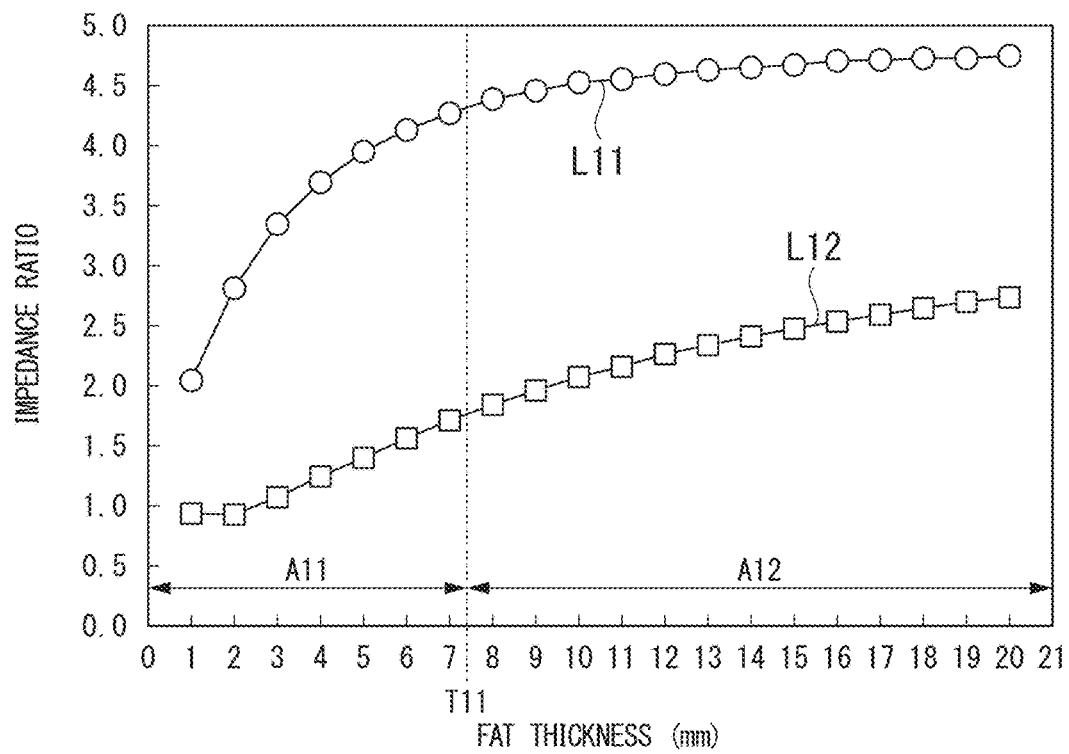
FIG. 13 is a graph showing a difference in impedance ratio due to a difference in the interval of the current injection electrodes in the embodiment.

FIG. 13 is a graph showing a difference in impedance ratio due to a difference in the interval of the current injection electrodes. In the graph shown in the drawing, the horizontal axis represents the fat thickness and the vertical axis represents the impedance ratio. As described above, the impedance ratio is a ratio of the bioelectrical impedance based on the current of the first frequency and the bioelectrical impedance based on the current of the second frequency. Specifically, a value which is obtained by dividing the bioelectrical impedance based on the current of the first frequency by the bioelectrical impedance based on the current of the second frequency is used as the impedance ratio.

A line L11 indicates an example of the impedance ratio in DR3-4. A line L12 indicates an example of the impedance ratio in DR1-4. As described above, the interval of the current injection electrodes in DR3-4 is 30 millimeter, but the interval of the current injection electrodes in DR1-4 is 70 millimeter. That is, the interval of the current injection electrodes in DR1-4 is larger.

Referring to FIG. 13, in a region A11 in which the fat thickness is equal to or less than T11, the line L11 has a larger slope than the line L12. Accordingly, when the fat thickness is equal to or less than T11, the fat thickness can be more accurately estimated using DR3-4. On the other hand, in a region A12 in which the fat thickness is larger (greater) than T11, the line L12 has a larger slope than the line L11. Accordingly, when the fat thickness is larger than T11, the fat thickness can be more accurately estimated using DR1-4.

Therefore, the fat thickness estimating unit 193 properly uses the intervals of the current injection electrodes.

For example, the storage unit 180 stores the relationship (e.g., first information) between the fat thickness and the impedance ratio based on DR3-4 which is indicated by the line L11 for the region A11. On the other hand, the storage unit stores the relationship (e.g., second information) between the fat thickness and the impedance ratio based on DR1-4 which is indicated by the line L12 for the region A12.

The fat thickness estimating unit 193 estimates the fat thickness using the impedance ratio correlated with the fat thickness in the fat thickness acquiring information among the impedance ratio based on DR1-4 and the impedance ratio based on DR3-4.

For example, when the fat thickness is 3 millimeter, the fat thickness estimating unit 193 acquires the impedance ratio 1.1 based on DR1-4 and the impedance ratio 3.4 based on DR3-4.

Among these, the impedance ratio 1.1 based on DR1-4 is included in the region A11 in the line L12. On the other hand, for the region A11, the storage unit 180 does not store the relationship between the fat thickness and the impedance ratio based on DR1-4 indicated by the line L12, and the fat thickness estimating unit 193 cannot convert the impedance ratio into the fat thickness.

On the other hand, the impedance ratio 3.4 based on DR3-4 is included in the region A11 in the line L11. The storage unit 180 stores the relationship between the fat thickness and the impedance ratio based on DR3-4 indicated by the line L11 for the region A11, and the fat thickness estimating unit 193 converts the impedance ratio into the fat thickness and acquires the estimated fat thickness value.

In this way, the fat thickness estimating unit 193 can convert the impedance ratio into the fat thickness on the basis of the line having a larger slope among the line L11 and the line L12 when the fat thickness is small and when the fat thickness is large, and it is thus possible to acquire a more accurate fat thickness.

As described above, the storage unit 180 stores the fat thickness acquiring information shown in FIG. 13 for each part of a body (for example, an abdomen or an upper arm). The fat thickness estimating unit 193 can more accurately estimate the fat thickness using the fat thickness acquiring information corresponding to a measurement part indicated by a user operation.

The number of current injection electrodes which are used to estimate the fat thickness by the fat thickness estimating system 1 is not limited to two pairs as described above. For example, the fat thickness estimating system 1 may measure a voltage value in DR2-4 in addition to DR1-4 and DR3-4 using the electrodes 222 and 227 as the current injection electrodes.

By using parts having better sensitivity (parts in which the measured voltage value greatly varies with the variation in the fat thickness) in the fat thickness acquiring information among the current injection electrodes, it is possible to more accurately estimate fat thickness.

The number of frequencies of the currents injected into a living body is not limited to two frequencies as described above, but may be three or more.

Securement of an appropriate contact state between the skin and the electrodes using the strain gauge 230 will be described below with reference to FIG. 14.

Figure 14:
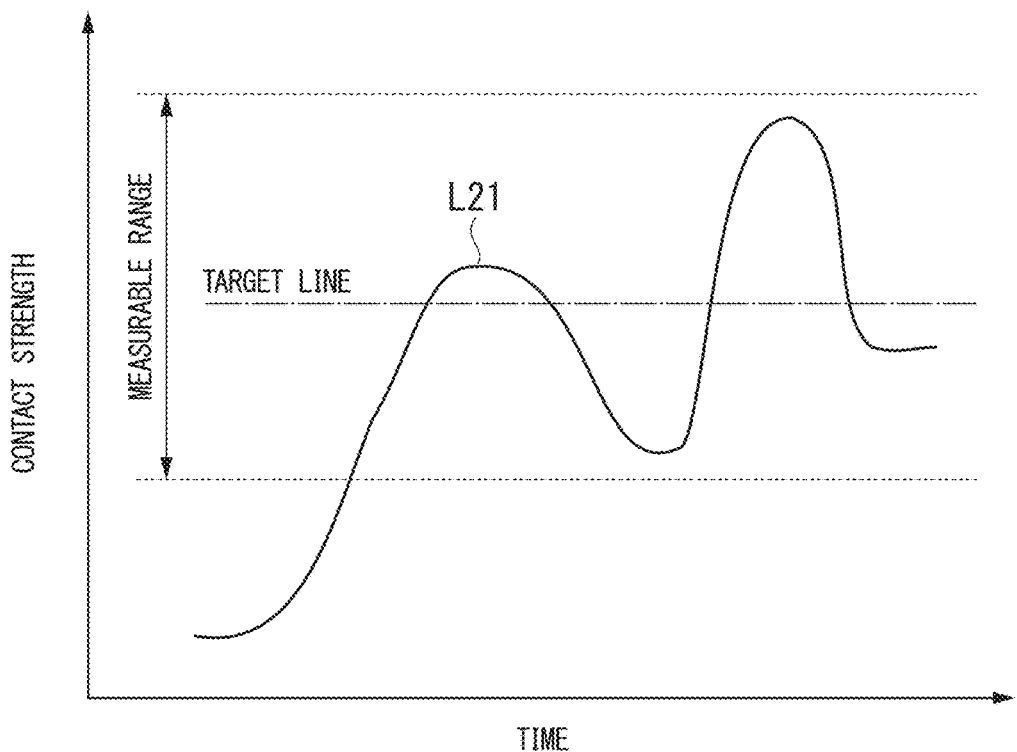
FIG. 14 is a diagram showing a display example of contact strength with which an impedance measuring unit comes in contact with a living body in the embodiment.

FIG. 14 is a diagram showing a display example of strength (for example, a pressure) with which the impedance measuring unit 200 comes in contact with a living body (a user's skin). In the drawing, the horizontal axis represents time and the vertical axis represents contact strength. A line L21 indicates strength with which the impedance measuring unit 200 comes in contact with the living body at each time.

As described above, a measured strain value measured by the strain gauge 230 can be used as a value indicating the strength with which the impedance measuring unit 200 comes in contact with the living body. The contact state detecting unit 192 detects a contact state of the electrodes, which are used to measure impedance of a target living body, with the living body by acquiring the measured strain value as contact state information.

The contact state detecting unit 192 displays a measurable range, or a target line, or both thereof on the display unit 120 in addition to the contact state information (the measured strain information) such as the line L21. Here, the measurable range or the target line is set in advance as a range or a value of contact strength in which impedance of a contact part between the electrode and the skin is relatively small.

A user adjusts a method of pressing the impedance measuring unit 200 against the skin such that the contact strength is included in the measurable range or such that the contact strength approaches the target line. Accordingly, the user can reduce the impedance of the contact part between the electrode and the skin by pressing the impedance measuring unit 200 against the skin with an appropriate pressure, and the measurement circuit 241 can more accurately measure the bioelectrical impedance.

The operation of the smartphone 100 will be described below with reference to FIG. 15.

Figure 15:
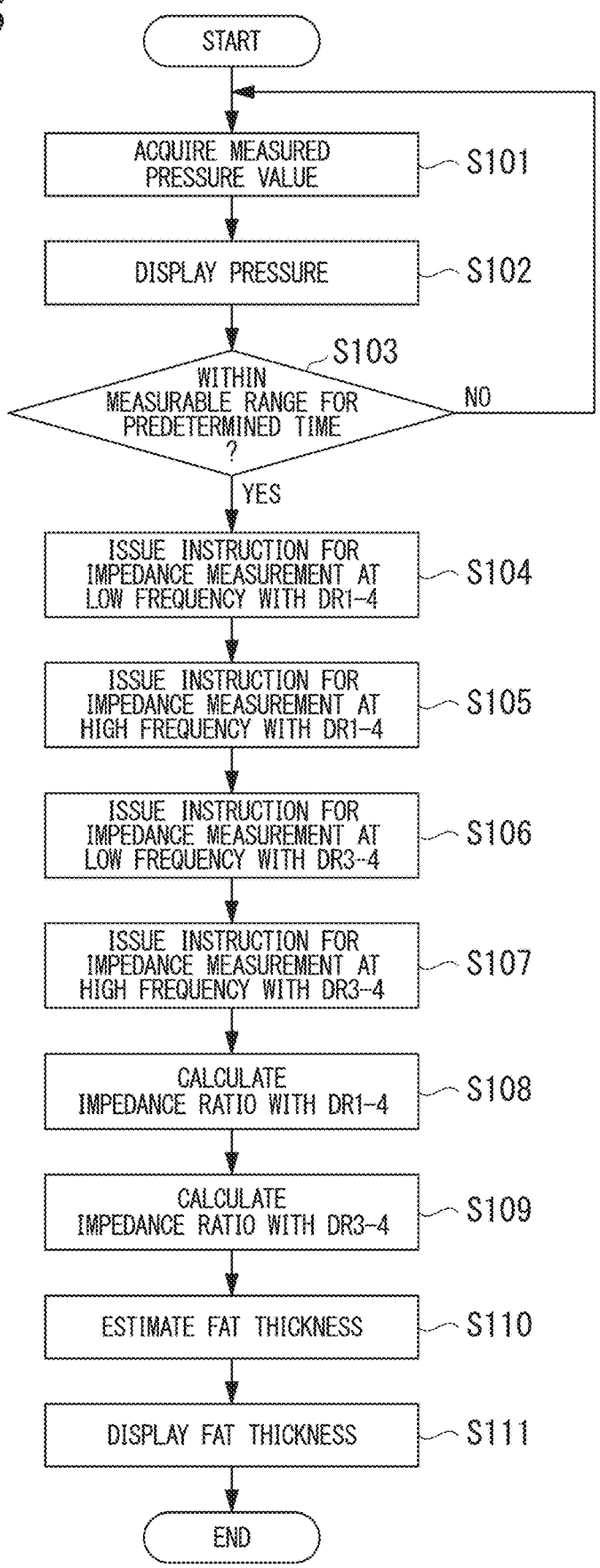
FIG. 15 is a flowchart showing an example of a process flow of causing a smartphone to estimate a fat thickness value in the embodiment.

FIG. 15 is a flowchart showing an example of a process flow of causing the smartphone 100 to estimate a fat thickness. For example, when a user operation instructing to measure a fat thickness is received by the operation input unit 130, the smartphone 100 starts the process flow shown in the drawing.

In the process flow shown in FIG. 15, the contact state detecting unit 192 acquires a measured pressure value (a measured strain value) measured by the strain gauge 230 from the impedance measuring unit 200 via the communication unit 110 (Step S101).

Then, the display unit 120 displays the measured pressure value measured by the strain gauge 230 as described above with reference to FIG. 14 (Step S102).

Then, the contact state detecting unit 192 determines whether a state in which the measured pressure value is in the measurable range is maintained for a predetermined time or more (Step S103). When it is determined that the state is not maintained for the predetermined time or more (NO in Step S103), the process flows is returned to Step S101.

On the other hand, when it is determined that the state is maintained for the predetermined time or more (YES in Step S103), the impedance measurement instructing unit 191 transmits an impedance measurement instruction to estimate a fat thickness with a current of a low frequency using the electrodes DR1-4 to the impedance measuring unit 200 via the communication unit 110, and the communication unit 110 acquires a measured impedance value (Step S104).

Then, the impedance measurement instructing unit 191 transmits an impedance measurement instruction to estimate a fat thickness with a current of a high frequency using the electrodes DR1-4 to the impedance measuring unit 200 via the communication unit 110 and the communication unit 110 acquires a measured impedance value (Step S105).

In addition, when it is determined that the state is maintained for the predetermined time or more (YES in Step S103), the impedance measurement instructing unit 191 transmits an impedance measurement instruction to estimate a fat thickness with a current of a low frequency using the electrodes DR3-4 to the impedance measuring unit 200 via the communication unit 110, and the communication unit 110 acquires a measured impedance value (Step S106).

Then, the impedance measurement instructing unit 191 transmits an impedance measurement instruction to estimate a fat thickness with a current of a high frequency using the electrodes DR3-4 to the impedance measuring unit 200 via the communication unit 110 and the communication unit 110 acquires a measured impedance value (Step S107).

The processes of Steps S104 to S107 can be performed in various orders.

Then, the fat thickness estimating unit 193 calculates an impedance ratio for DR1-4 by dividing the measured impedance value acquired in Step S104 by the measured impedance value acquired in Step S105 (Step S108).

In addition, the fat thickness estimating unit 193 calculates an impedance ratio for DR3-4 by dividing the measured impedance value acquired in Step S106 by the measured impedance value acquired in Step S107 (Step S109).

Then, the fat thickness estimating unit 193 acquires an estimated fat thickness value using the impedance ratio acquired in Step S108, the impedance ratio acquired in Step S109, and the fat thickness acquiring information stored in the storage unit 180 as described above with reference to FIG. 13 (Step S110).

Then, the display unit 120 displays the estimated fat thickness value acquired in Step S110 (Step S111).

Thereafter, the process flow shown in FIG. 15 ends.

As described above, the fat thickness estimating unit 193 estimates the fat thickness in the target living body on the basis of the ratio of the measured impedance value based on the current of the first frequency and the measured impedance value based on the current of the second frequency higher than the first frequency and the fat thickness acquiring information.

Accordingly, the fat thickness estimating unit 193 can reduce an influence of the contact state of the fat thickness estimation electrode 220 with the skin to the impedance and can more accurately estimate the fat thickness. In this way, according to the fat thickness estimating unit 193, it is possible to reduce a decrease in fat thickness estimation accuracy due to a variation of the contact state of the electrode with the living body.

The contact state detecting unit 192 detects the contact state of the electrode, which is used to measure the impedance of the target living body, with the living body. The display unit 120 displays the detection result of the contact state by the contact state detecting unit 192 along a time as in the example shown in FIG. 14.

Accordingly, the user adjusts a method of pressing the impedance measuring unit 200 against the skin such that the contact strength is included in the measurable range or such that the contact strength approaches the target line. Accordingly, the user can reduce the impedance of the contact part between the electrode and the skin by pressing the impedance measuring unit 200 against the skin with an appropriate pressure, and the measurement circuit 241 can more accurately measure the bioelectrical impedance.

The moisture estimating unit 194 estimates the degree of moisture of the skin of the living body on the basis of the measured bioelectrical impedance value.

In this way, by causing the smartphone 100 to acquire the degree of moisture of the skin in addition to the fat thickness, the user can easily measure the degree of moisture. The moisture of the skin varies from time to time, but the user can simply measure the degree of moisture of the skin using the fat thickness estimating system 1 and thus can take countermeasures such as moisturization if necessary.

The impedance measuring unit 200 includes a plurality of pairs of current injection electrodes having different intervals. The storage unit 180 stores information indicating relationships each between fat thickness and impedance ratio based on any one pair of the plurality of pairs of current injection electrodes, which is selected for according to fat thickness, as the fat thickness acquiring information. The fat thickness estimating unit 193 estimates the fat thickness in the target living body on the basis of the ratio correlated with the fat thickness in the fat thickness acquiring information among the impedance ratios based on the plurality of pairs of current injection electrodes.

Accordingly, as described above with reference to FIG. 13, the fat thickness estimating unit 193 can more accurately estimate the fat thickness when the fat thickness is small and when the fat thickness is large.

The method of causing the contact state detecting unit 192 to detect the contact state of the electrode, which is used to measure the impedance of the target living body, with the living body is not limited to the method using the strain gauge 230.

For example, the contact state detecting unit 192 may calculate a variation coefficient of the measured impedance value of the target living body or a value based on the measured impedance value (for example, an impedance ratio).

For example, the contact state detecting unit 192 acquires the measured impedance value measured by the measurement circuit 241 for a predetermined time, and calculates a standard deviation of impedance $\sigma$ and an average value of impedance $\mu$. The contact state detecting unit 192 calculates the variation coefficient CV by applying the acquired standard deviation $\sigma$ or the average value $\mu$ to Equation (1).

$$CV = \frac{\sigma}{\mu} \quad (1)$$

Then, the display unit 120 displays the variation coefficient CV along a time.

When the variation of the measured impedance value or the value based on the measured impedance value is great, the variation coefficient CV also increases. When the variation of the measured impedance value or the value based on the measured impedance value is small, the variation coefficient CV also decreases. Particularly, when the contact state (a close contact state) between the skin and the electrode is good, the variation coefficient decreases.

Therefore, the user can press the impedance measuring unit 200 against the skin with an appropriate pressure to reduce the impedance of the contact part with the skin by adjusting the method of pressing the impedance measuring unit 200 against the skin. Accordingly, the fat thickness estimating unit 193 can more accurately estimate the fat thickness.

The type of the impedance measuring unit 200 is not limited to the type shown in FIG. 2. For example, the impedance measuring unit 200 may be sewn to a shirt. Accordingly, the user can easily understand, for example, a variation in subcutaneous fat before and after running.

In this embodiment, the fat thickness is estimated on the basis of the ratio of impedance at different frequencies, but a ratio of impedance in different conditions other than the frequency may be calculated.

For example, the fat thickness estimating system 1 (the fat thickness estimating unit 193) may estimate a fat thickness on the basis of a ratio of impedance which is acquired by injecting a current from pairs of electrodes having different intervals.

For example, the impedance measuring unit 200 measures skin impedance using electrodes having a small interval such as the moisture estimation electrodes 210 shown in FIG. 2 in addition to measurement of the impedance using the pair of electrodes having a fat thickness measurement interval such as DR1-4 or DR3-4. In this measurement of skin impedance, impedance of the surface part of a living body is measured and the impedance is not affected well by a deep part. Accordingly, the impedance is not affected well by the fat thickness.

The fat thickness estimating unit 193 converts a value (a ratio), which is obtained by dividing the measured impedance value at the electrode interval for measurement of a fat thickness by the measured impedance value measured by the electrodes having a small interval, into the fat thickness on the basis of the fat thickness acquiring information.

In this way, the storage unit 180 stores the fat thickness acquiring information indicating a relationship between a ratio of the bioelectrical impedance in the first condition and the bioelectrical impedance in the second condition and the fat thickness. The storage unit 110 acquires the measured impedance value in the first condition and the measured impedance value in the second condition for the target living body. The fat thickness estimating unit 193 calculates the fat thickness in the target living body on the basis of the ratio of the measured impedance value in the first condition and the measured impedance value in the second condition and the fat thickness acquiring information.

Accordingly, in the fat thickness estimating system 1, normalization (standardization) of calculating the ratio of the measured impedance values corresponding to the fat thickness with a measured impedance value, which is not affected well by the difference in the fat thickness, as a reference value can be carried out.

By the normalization, the fat thickness estimating unit 193 can reduce an influence of the contact state of the fat thickness estimation electrode 220 with the skin to the impedance and can more accurately estimate the fat thickness. In this way, according to the fat thickness estimating unit 193, it is possible to reduce a decrease in fat thickness estimation accuracy due to a variation in the contact state between the electrode and the living body.

In this case, similarly to the case in which the impedance at different frequencies is used, various values indicating impedance such as a measured voltage value can be used as the measured impedance value.

Additionally and/or alternatively, the fat thickness estimating unit 193 and the moisture estimating unit 194 can estimate a value in an equilibrium state (a stable value) on the basis of variation in a value (a variation trend) within a predetermined time for the purpose of shortening a process time.

The processes of the functional units may be performed by recording a program for embodying all or some functions of the control unit 190 on a computer-readable recording medium and causing a computer system to read and execute the program recorded on the recording medium. The "computer system" mentioned herein includes an operating system (OS) or hardware such as peripherals.

When a WWW system is used, the "computer system" includes a homepage providing environment (or a homepage display environment).

Examples of the "computer-readable recording medium" include a portable medium such as a flexible disk, a magneto-optical disc, a ROM, or a CD-ROM and a storage device such as a hard disk built in the computer system. The "computer-readable recording medium" may include a medium that dynamically holds a program for a short time like a communication line when a program is transmitted via a network such as the Internet or a communication line such as a telephone circuit or a medium that holds a program for a predetermined time like a volatile memory in a computer system serving as a server or a client in that case. The program may embody some of the above-mentioned functions or may embody the above-mentioned functions in combination with a program which has been recorded in advance in the computer system.

While embodiments of the present invention have been described above with reference to the accompanying drawings, specific configurations thereof are not limited to the embodiments but include design changes not departing from the gist of the present invention.

DESCRIPTION OF THE REFERENCE SYMBOLS

1 Fat thickness estimating system
100 Smartphone (portable information terminal, tablet terminal, mobile computer)
110 Communication unit
120 Display unit
130 Operation input unit
180 Storage unit
190 Control unit
191 Impedance measurement instructing unit
192 Contact state detecting unit
193 Fat thickness estimating unit
194 Moisture estimating unit
200 Impedance measuring unit
210 Moisture estimation electrode
220 Fat thickness estimation electrode
230 Strain gauge
240 Measurement and communication unit
241 Measurement circuit
242 Communication circuit

The invention claimed is:

1. A system comprising:
a device including at least two detection electrodes and at least four application electrodes,
a memory; and
a processor, wherein,
the application electrodes includes:
a first combination of the application electrodes, which are arranged with a first interval therebetween, and
a second combination of the application electrodes, which are arranged with a second interval therebetween, the second interval being different from the first interval,
the memory stores information includes (a) first information indicating relationship between fat thickness and ratio of bioelectrical impedance at a first frequency and bioelectrical impedance at a second frequency in the first combination and (b) second information indicating relationship between fat thickness and ratio of bioelectrical impedance at the first frequency and bioelectrical impedance at the second frequency in the second combination, the second frequency being different from the first frequency,
the device measures impedance of a target living body at the first frequency and impedance of the target living body at the second frequency,
the processor, in communication with the device and the memory, uses one of the first information and the second information to estimate a fat thickness value of the target living body based on the stored information and on a ratio of the measured impedance value at the first frequency and the measured impedance value at the second frequency, the first information being used when the fat thickness value is smaller than the predetermined value, the second information being used when the fat thickness value is greater than the predetermined value.

2. The system according to claim 1, further comprising:
a main body on which the electrodes are provided,
a detector provided on the main body to detect a contact state of the electrodes with the living body; and
the display displays a detection result of the detector along a time.

3. The system according to claim 1, wherein
the processor that detects a variation coefficient of the measured impedance value of the target living body or of a value based on the measured impedance value, and
the system further comprises a display that displays the variation coefficient.

4. The system according to claim 1, wherein the processor estimates a degree of moisture of skin of the living body on the basis of the measured impedance value of the living body.

5. The system according to claim 1, wherein the detection electrodes and the application electrodes are arranged in a line.

6. The system according to claim 1, wherein
the second combination of the application electrodes is arranged inside the first combination of the application electrodes, and
the detection electrodes are arranged inside the second combination of the application electrodes.

7. The system according to claim 1, wherein
the device include a main body on which the electrodes are provided, and
the main body is deformable in a shape substantially corresponding to an outline of the target living body.

8. The system according to claim 1, wherein
the application electrodes further includes a third combination of the application electrodes, which are arranged with a third interval therebetween, the third interval being different from the second interval and the first interval.

9. The system according to claim 1, wherein
the device further measures impedance of the target living body at a third frequency that is different from the first frequency and the second frequency.

10. A method comprising:
acquiring a measured impedance value, from a device, of a target living body at a first frequency and a measured impedance value of the target living body at a second frequency; and
estimating a fat thickness value of the target living body based on stored information and on a ratio of the measured impedance value at the first frequency and the measured impedance value at the second frequency, wherein the device includes at least two detection electrodes and at least four application electrodes, the application electrodes includes:
- a first combination of the application electrodes, which are arranged with a first interval therebetween,
- a second combination of the application electrodes, which are arranged with a second interval therebetween, the second interval being different from the first interval, the stored information includes (a) first information indicating relationship between fat thickness and ratio of bioelectrical impedance at the first frequency and bioelectrical impedance at the second frequency in the first combination and (b) second information indicating relationship between fat thickness and ratio of bioelectrical impedance at the first frequency and bioelectrical impedance at the second frequency in the second combination, and the estimation of fat thickness including using one of the first information and the second information to estimate the fat thickness value of the target living body, the first information being used when the fat thickness value is smaller than a predetermined value, the second information being used when the fat thickness value is greater than the predetermined value.

11. A non-transitory computer-readable storage medium storing instructions executable by a computer to perform functionality corresponding to the steps comprising:

acquiring a measured impedance value, from a device, of a target living body at a first frequency and a measured impedance value of the target living body at a second frequency; and estimating a fat thickness value of the target living body based on stored information and on a ratio of the measured impedance value at the first frequency and the measured impedance value at the second frequency, wherein the device includes at least two detection electrodes and at least four application electrodes, the application electrodes includes:
- a first combination of the application electrodes, which are arranged with a first interval therebetween,
- a second combination of the application electrodes, which are arranged with a second interval therebetween, the second interval being different from the first interval, the stored information includes (a) first information indicating relationship between fat thickness and ratio of bioelectrical impedance at the first frequency and bioelectrical impedance at the second frequency in the first combination and (b) second information indicating relationship between fat thickness and ratio of bioelectrical impedance at the first frequency and bioelectrical impedance at the second frequency in the second combination, and the estimation of fat thickness including using one of the first information and the second information to estimate the fat thickness value of the target living body, the first information being used when the fat thickness value is smaller than a predetermined value, the second information being used when the fat thickness value is greater than the predetermined value.

* * * * *